(12) United States Patent
Li et al.

(10) Patent No.: US 11,536,752 B2
(45) Date of Patent: Dec. 27, 2022

(54) HIGH VOLTAGE ASSEMBLY AND DETECTOR

(71) Applicant: Neusoft Medical Systems Co., Ltd., Liaoning (CN)

(72) Inventors: Shuangxue Li, Liaoning (CN); Xin Xiang, Liaoning (CN); Xiaoqing Hu, Liaoning (CN); Songbo Yang, Liaoning (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 233 days.

(21) Appl. No.: 17/152,420

(22) Filed: Jan. 19, 2021

(65) Prior Publication Data

US 2021/0223294 A1 Jul. 22, 2021

(30) Foreign Application Priority Data

Jan. 20, 2020 (CN) .......................... 202010066015.3

(51) Int. Cl.
| | |
|---|---|
| *G01R 19/00* | (2006.01) |
| *G01R 1/02* | (2006.01) |
| *G01R 1/04* | (2006.01) |
| *G01R 1/067* | (2006.01) |
| *G01R 1/073* | (2006.01) |
| *A61B 6/00* | (2006.01) |
| *A61B 6/03* | (2006.01) |

(52) U.S. Cl.
CPC ........ *G01R 19/0046* (2013.01); *A61B 6/4241* (2013.01); *A61B 6/4266* (2013.01); *G01R 1/06777* (2013.01); *A61B 6/035* (2013.01)

(58) Field of Classification Search
CPC . G01R 19/00; G01R 1/02; G01R 1/04; G01R 1/067; G01R 1/073; A61B 6/00
See application file for complete search history.

(56) References Cited

U.S. PATENT DOCUMENTS

2008/0157255 A1* 7/2008 Kominami .......... H01L 31/1832
257/E31.022

* cited by examiner

*Primary Examiner* — Neel D Shah
(74) *Attorney, Agent, or Firm* — Fish & Richardson P.C.

(57) ABSTRACT

High voltage assemblies and detectors are provided. In one aspect, a high voltage assembly includes a high voltage base board and a plurality of sub-detectors. Each sub-detector includes a crystal substrate, a crystal, a high voltage transfer board, and a high voltage cathode board. One of the high voltage transfer board and the high voltage base board includes first and second connection members, and the other one includes first and second contact members. The first connection member is configured to shift relative to the first contact member in response to a first force, and the second connection member is configured to shift relative to the second contact member in response to a second force. A high voltage is applied at both ends of the crystal through electrically contacting the first connection member with the first contact member and electrically contacting the second connection member with the second contact member.

20 Claims, 3 Drawing Sheets

HIGH VOLTAGE ASSEMBLY AND DETECTOR

CROSS REFERENCE TO RELATED APPLICATIONS

This application claims priority to Chinese Patent Application No. 202010066015.3 entitled "HIGH VOLTAGE ASSEMBLY AND DETECTOR" filed on Jan. 20, 2020, the entire content of which is incorporated herein by reference.

TECHNICAL FIELD

The present disclosure relates to medical device technology, and in particular to high voltage assemblies and detectors.

BACKGROUND

A photon-counting multi-spectral CT (Computed Tomography) detector includes a plurality of sub-detectors with energy direct transfer materials (such as crystalline semiconductors). For such a crystalline semiconductor detector, a pair of thousand volts of bias high voltages needs to be applied to upper and lower sides of the crystal to form a stable strong electric field in the crystal. However, wiring for thousand volts of high voltages is very difficult, which brings challenges to system design.

SUMMARY

One aspect of the present disclosure features a high voltage assembly, including: a high voltage base board and a plurality of sub-detectors configured to be in electrical contact with the high voltage base board. Each of the plurality of sub-detectors includes: a crystal substrate, a crystal coupled to an anode of the crystal substrate, a high voltage transfer board coupled to the crystal substrate, and a high voltage cathode board configured to couple the crystal with the high voltage transfer board. One of the high voltage transfer board and the high voltage base board includes a first connection member and a second connection member, and the other one of the high voltage transfer board and the high voltage base board includes a first contact member and a second contact member. The first connection member is configured to shift relative to the first contact member in response to a first force, and the second connection member is configured to shift relative to the second contact member in response to a second force. The high voltage transfer board and the high voltage base board are configured to be in electrical contact with the first contact member through the first connection member and are configured to be in electrical contact with the second contact member through the second connection member, such that a high voltage is applied at both ends of the crystal.

In some embodiments, the crystal includes a cadmium telluride (CdTe) crystal or a cadmium zinc telluride (CZT) crystal.

In some embodiments, the sub-detector further includes a data acquisition board coupled to the crystal substrate.

In some embodiments, the crystal substrate includes an ASIC (Application Specific Integrated Circuit) chip configured to acquire and process a pulse signal and transmit the pulse signal to the data acquisition board.

In some embodiments, the sub-detector further includes a support configured to support the crystal substrate, the high voltage transfer board, and the data acquisition board.

In some embodiment, the sub-detector further includes a high voltage connection component. The high voltage transfer board includes the first connection member and the second connection member, the high voltage cathode board is coupled with the first connection member through the high voltage connection component, and the crystal substrate is coupled with the second connection member through the data acquisition board. The first connection member is coupled to a cathode of the high voltage base board, and the second connection member is coupled to an anode of the high voltage base board.

In some embodiment, the high voltage cathode board includes a bare electrode arranged on a first side of the high voltage cathode board and an insulating material arranged on a second side of the high voltage cathode board.

In some embodiment, the bare electrode is attached to the crystal, and the high voltage cathode board is made of a soft conductive material.

In some embodiment, the soft conductive material includes a first film and a second conductive metal film that are laminated together, and the second conductive metal film is attached to the crystal.

In some embodiment, at least one of the first contact member or the second contact member includes an electrically conductive pad.

In some embodiment, the at least one of the first connection member or the second connection member includes a Pogo Pin terminal or an elastically deformable elastic terminal.

In some embodiment, the high voltage base board includes a high voltage area and a low voltage area, and the high voltage base board includes the first contact member and the second contact member, and the first contact member and the second contact member are arranged in the high voltage area.

In some embodiment, the high voltage assembly further includes a spacer made of an insulating material, and the spacer is provided between the first contact member and the second contact member.

Another aspect of the present disclosure features a detector, including a cradle and a high voltage assembly. The high voltage assembly includes: a high voltage base board fixed to the cradle and a plurality of sub-detectors configured to be in electrical contact with the high voltage base board. Each of the plurality of sub-detectors includes: a crystal substrate, a crystal coupled to an anode of the crystal substrate, a high voltage transfer board coupled to the crystal substrate, and a high voltage cathode board configured to couple the crystal with the high voltage transfer board. One of the high voltage transfer board and the high voltage base board includes a first connection member and a second connection member, and the other one of the high voltage transfer board and the high voltage base board includes a first contact member and a second contact member. The first connection member is configured to shift relative to the first contact member in response to a first force, and the second connection member is configured to shift relative to the second contact member in response to a second force. The high voltage transfer board and the high voltage base board is configured to be in electrical contact with the first contact member through the first connection member and is configured to be in electrical contact with the second contact member through the second connection member, such that a high voltage is applied at both ends of the crystal. One of the cradle and the sub-detector includes a hole, and the other one of the cradle and the sub-detector includes a protrusion that matches with the hole, and the sub-detector is fixed to the cradle through the hole and the protrusion.

In some embodiments, the sub-detector further includes a data acquisition board coupled to the crystal substrate.

In some embodiments, the sub-detector further includes a high voltage connection component. The high voltage transfer board includes the first connection member and the second connection member, the high voltage cathode board is coupled with the first connection member through the high voltage connection component, and the crystal substrate is coupled with the second connection member through the data acquisition board. The first connection member is coupled to a cathode of the high voltage base board, and the second connection member is coupled to an anode of the high voltage base board.

In some embodiment, the high voltage cathode board includes a bare electrode arranged on a first side of the high voltage cathode board, and an insulating material arranged on a second side of the high voltage cathode board.

In some embodiment, the bare electrode is attached to the crystal, and the high voltage cathode board is made of a soft conductive material.

In some embodiment, at least one of the first contact member or the second contact member includes an electrically conductive pad.

In some embodiment, the at least one of the first connection member or the second connection member includes a Pogo Pin terminal or an elastically deformable elastic terminal.

The exemplary embodiments will be described in detail here, and examples thereof are illustrated in the accompanying drawings. When the following description refers to the accompanying drawings, unless otherwise stated, the same reference signs in different drawings designate the same or similar elements. The implementation manners described in the following exemplary embodiments do not represent all implementation manners consistent with the present application. On the contrary, they are merely examples of devices and methods consistent with some aspects of the present application as defined in the appended claims.

High voltage assemblies and detectors according to embodiments of the present disclosure will be described in detail below with reference to the accompanying drawings. In some embodiments, the term "high voltage" refers to a voltage higher than 100 Volts (Vs). For example, a working Direct Current (DC) voltage supplied to a crystal is much higher than a working DC voltage of an electronic circuit active chip, and can be at least up to several hundred Volts (Vs). The term "low voltage" refers to a voltage lower than or equal to 5 Vs. For example, a working DC voltage of the electronic circuit active chip is lower than or equal to 5 Vs.

DETAILED DESCRIPTION

Figure 1:
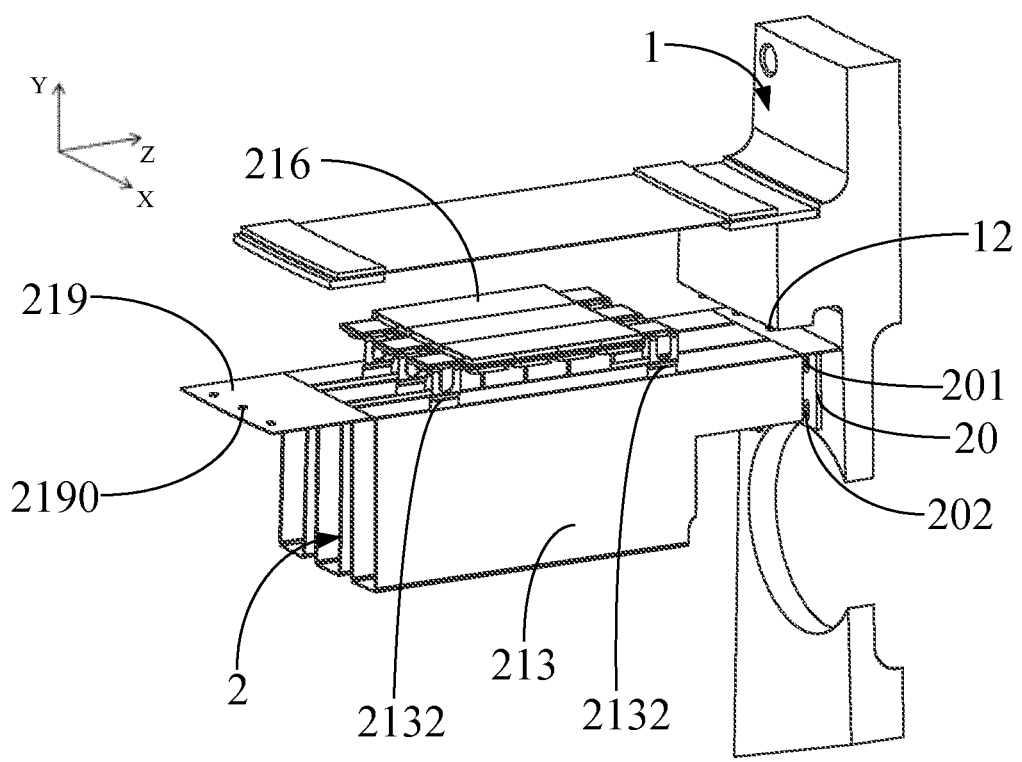
FIG. 1 is a perspective view of a structure obtained by assembling a high voltage assembly and a cradle according to an embodiment of the present disclosure, and only a part of the cradle is shown to clearly show a structure of the high voltage assembly.
Figure 2:
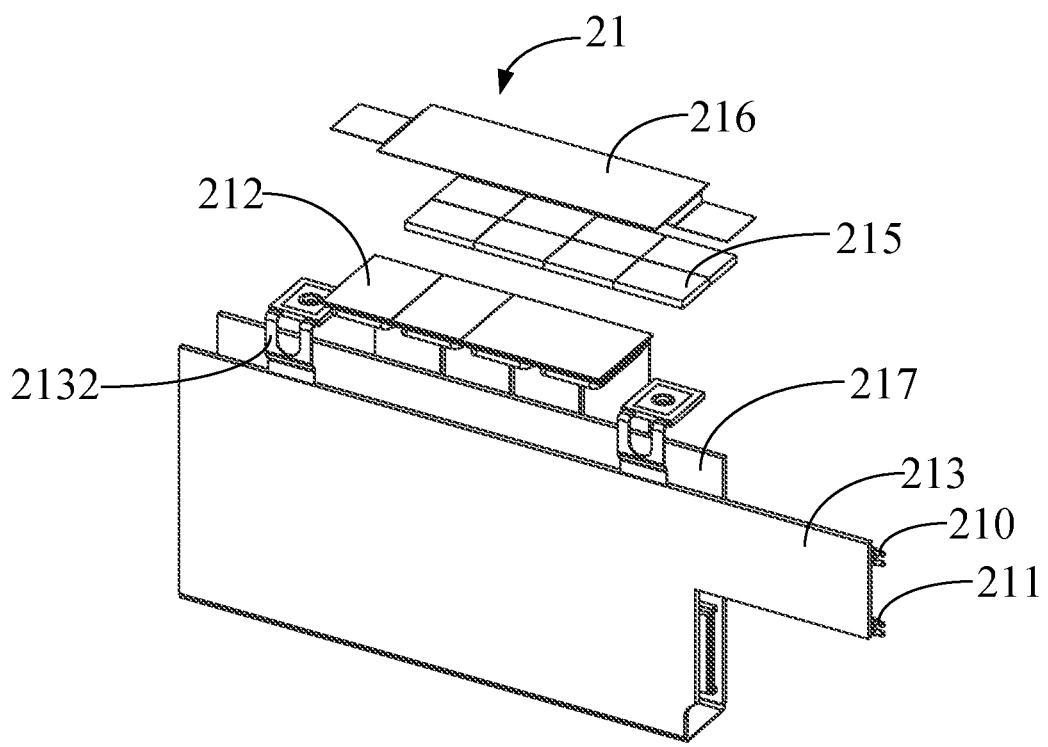
FIG. 2 is an exploded schematic diagram of the sub-detector shown in FIG. 1.
Figure 3:
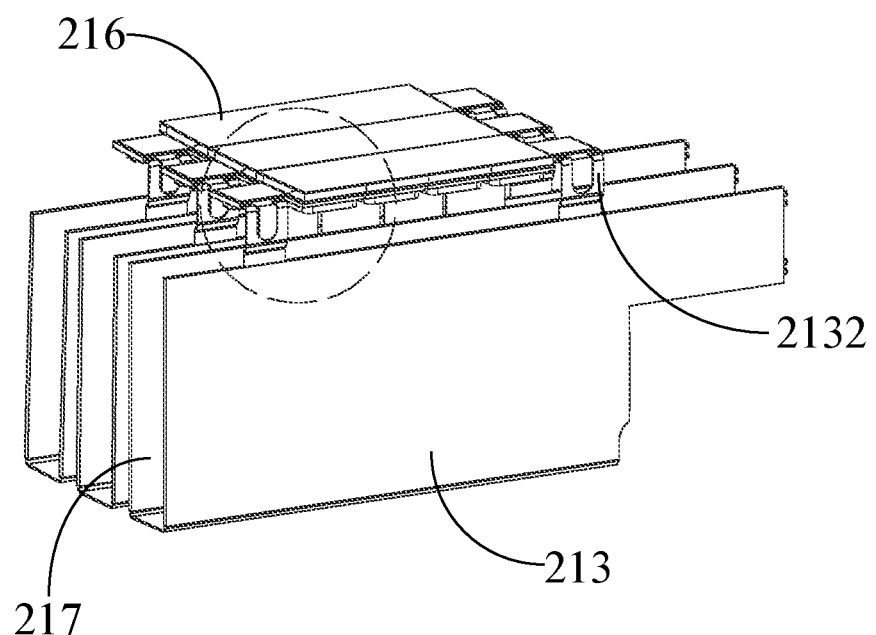
FIG. 3 is a schematic diagram of a structure obtained by assembling a plurality of sub-detectors shown in FIG. 2.
Figure 4:
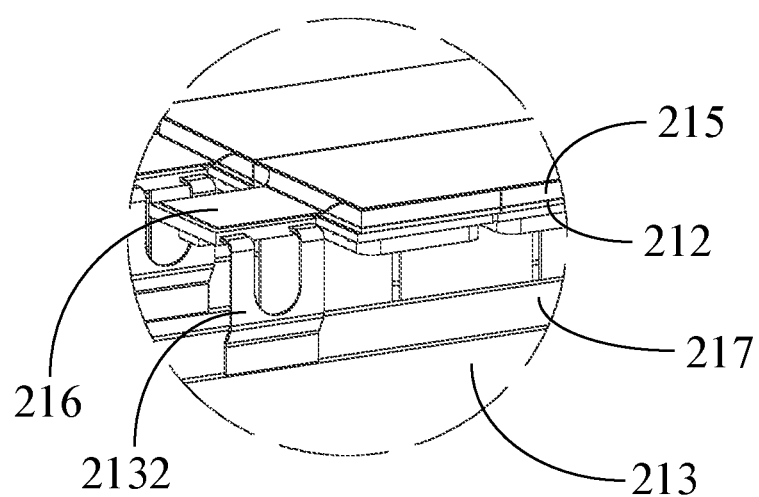
FIG. 4 is an enlarged view of a circle portion shown in FIG. 3.

FIGS. 1 to 4 illustrate a detector according to one or more embodiments of the present disclosure. The detector includes a cradle 1 and a high voltage assembly 2 fixed to the cradle 1.

The high voltage assembly 2 includes a high voltage base board 20 and a plurality of sub-detectors 21 in electrical contact with the high voltage base board 20. The high voltage base board 20 is fixed to the cradle 1. The plurality of sub-detectors 21 have the same structure. The high voltage base board 20 includes a first contact member 201 and a second contact member 202. The first contact member 201 is a cathode and the second contact member 202 is an anode, or the first contact member 201 is an anode and the second contact member 202 is a cathode. The sub-detector 21 includes a first connection member 210 electrically coupled to the first contact member 201 and a second connection member 211 electrically coupled to the second contact member 202. In some embodiments, the first contact member 201 and the second contact member 202 are electrically conductive pads. In some other embodiments, the first contact member 201 and the second contact member 202 may be any other electrically conductive components.

The sub-detector 21 and the high voltage base board 20 can be elastically coupled through the first connection member 210 and the second connection member 211. For example, the first connection member 210 and/or the second connection member 211 includes elastically deformable elastic terminals or Pogo Pin terminals. The detector includes the plurality of sub-detectors 21, and ideally, the gaps between every two adjacent sub-detectors 21 should be consistent. However, due to machining errors, the position of the sub-detector 21, especially the Z-direction position, can be fine-tuned during the installation process, so as to ensure that the gaps between any two adjacent sub-detectors 21 are consistent. In embodiments of the present disclosure, the sub-detector 21 of the high voltage assembly 2 and the high voltage base board 20 can be elastically contacted by the first connection member 210 and the second connection member 211, so as to conveniently adjust the position of the sub-detector 21 and effectively ensure the relative consistency of the positions of the plurality of sub-detectors 21.

Figure 5:
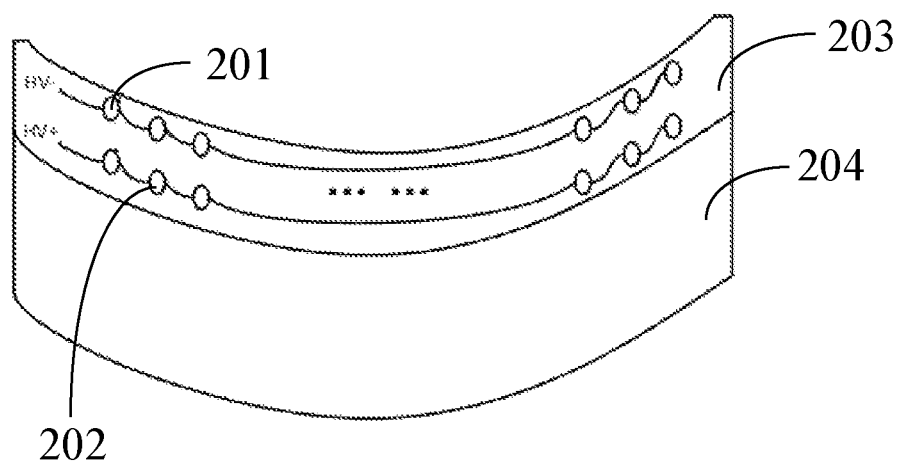
FIG. 5 is a structure schematic diagram of a high voltage base board according to an embodiment of the present disclosure.

For each of the plurality of sub-detectors 21, the high voltage base board 20 may include a first connection member 210 and/or a second connection member 211, and correspondingly, the sub-detector 21 includes a first contact member 201 and/or a second contact member 202. For the plurality of sub-detectors 21, a plurality of first connection members 210 and/or a plurality of first contact members 201 are arranged in an arc shape, and a plurality of second connection members 211 and/or a plurality of second contact members 202 are arranged in an arc shape. For example, the plurality of first connection members 210 are arranged in an arc on the XY plane. The high voltage base board 20 is correspondingly arranged in an arc shape, as shown in FIG. 5, so as to effectively ensure that the first connection member 210 is in stable contact with the first contact member 201 and the second connection member 211 is in stable contact with the second contact member 202.

The sub-detector 21 includes a crystal substrate 212, a high voltage transfer board 213, a crystal 215 coupled to the crystal substrate 212, a high voltage cathode board 216 located on one side of the crystal substrate 212, a high voltage connection component 2132 coupling the high voltage cathode board 216 and the high voltage transfer board 213, and a data acquisition board 217 coupled to the crystal substrate 212 and the high voltage transfer board 213. The sub-detector 21 can include one or more high voltage connection components 2132. The first connection member 210 is coupled with the high voltage cathode board 216 through the high voltage connection component 2132. In an embodiment of the present disclosure, the high voltage connection component 2132 includes a circuit board, for example, a flexible circuit board. In an embodiment of the present disclosure, the high voltage connection component 2132 includes a cable.

The high voltage cathode board 216 includes a bare electrode arranged on one side of the high voltage cathode board 216 and an insulating material arranged on the other side of the high voltage cathode board 216. The bare electrode is attached to one end of the crystal 215, and the high voltage cathode board 216 is coupled to the first connection member 210. The other end of the crystal 215 is coupled to an anode of the crystal substrate 212, the anode of the crystal substrate 212 is coupled to the data acquisition board 217, and the data acquisition board 217 is coupled to the second connection member 211.

In an embodiment of the present disclosure, the high voltage transfer board 213 includes a circuit board, including but not limited to a Printed Circuit Board (PCB). The high voltage transfer board 213 includes the first connection member 210 and the second connection member 211. The first connection member 210 is electrically coupled to the first contact member 201 of the high voltage base board 20, and the second connection member 211 is electrically coupled to the second contact member 202 of the high voltage base board 20, so that the sub-detector 21 can obtain a high voltage power from the high voltage base board 20. The first connection member 210 is coupled to the cathode of the high voltage base board 20, and the second connection member 211 is coupled to the anode of the high voltage base board 20. Therefore, a high voltage is applied to both ends of the crystal 215 by the high voltage base board 20. The anode of the crystal substrate 212 receives the signal output of the crystal 215.

A bias high voltage is applied to both ends of the crystal 215 by the high voltage base board 20 to form an electric field, such that the crystal 215 receives radiation photons to generate and acquire pulse signals. The crystal substrate 212 can include an ASIC (Application Specific Integrated Circuit) chip configured to acquire and process a pulse signal and transmit the pulse signal to the data acquisition board 217. The crystal 215 can include a cadmium telluride (CdTe) crystal or a cadmium zinc telluride (CZT) crystal, etc. Cadmium zinc telluride (CZT) is a compound of cadmium, zinc and tellurium, and can be an alloy of an alloy of cadmium telluride (CdTe) and zinc telluride (ZnTe).

The high voltage cathode board 216 may be made of a soft (or elastically) conductive material, e.g., with a relatively small value of Young's modulus. When there is a collision, the soft high voltage cathode board 216 can play a buffering role, thereby avoiding the damage of the crystal 215, and simplifying the equipment process because no additional buffer layer is needed. In an embodiment of the present disclosure, the soft (or elastically) conductive material includes a film and a conductive metal film, the conductive metal film is laminated on the film. The film may be a polyester (PET) film or a Kapton film or the like. The conductive metal film may be an aluminum film or the like. The conductive metal film is attached to the crystal 215.

The height of the free end of the first connection member 210 and/or the second connection member 211 is h1 before contacting with the high voltage base board 20. The height of the free end of the first connection member 210 and/or the second connection member 211 is h2 after contacting with the high voltage base board 20. The ratio of h2 to h1 is less than or equal to 0.5, and the elastic force generated by the compression of the first connection member 210 and the second connection member 211 can effectively ensure the contact stability between the high voltage transfer board 213 and the high voltage base board 20. The first connection member 210 is configured to shift relative to the first contact member 201 in response to a force, and the second connection member 211 is configured to shift relative to the second contact member 202 in response to a force. The configuration of the first connection member 210 and the second connection member 211 can thereby prevent a distance between the first connection member 210 of the individual sub-detector 21 and the first contact member 201 of the high voltage base board 20 or a distance between the second connection member 211 of the individual sub-detector 21 and the second contact member 202 of the high voltage base board 20 from changing due to a manufacturing tolerance or a slight position change, and thus avoid a situation that the connection member and the contact member cannot be contacted. This configuration can also effectively ensure that all sub-detectors 21 can be in stable electrical contact with the high voltage base board 20, and effectively ensure the quality of the image. Moreover, the cost of the first connection member 210 and the second connection member 211 is lower, which can reduce the cost of the detector.

The sub-detector 21 includes a support 219 configured to support the crystal substrate 212, the high voltage transfer board 213, and the data acquisition board 217. In some embodiments, the support 219 includes a hole 2190, for example, a through hole, and the cradle 1 includes a protrusion 12 accommodated to the hole 2190. The sub-detector 21 can be fixed to the cradle 1 by the hole 2190 and the protrusion 12. The protrusion 12 can be matched with the hole 2190, which can also effectively ensure the accurate alignment of the first connection member 210 with the first contact member 201 and the second connection member 211 with the second contact member 202. In some other embodiments, the cradle 1 may include the hole 2190, and correspondingly, the support 219 includes the protrusion 12. The plurality of sub-detectors 21 can be fixed to the cradle 1 through the support 219, so that no additional fixed device is required, the structure is simple, the cost is saved and the assembly is convenient.

Referring to FIG. 5, the high voltage base board 20 may include a high voltage area (i.e., region) 203 and a low voltage area 204, and a distance between the high voltage area 203 and the low voltage area 204 may be a preset safe insulation distance. In a case that the high voltage base board 20 includes the first contact member 201 and the second contact member 202, the first contact member 201 and the second contact member 202 are disposed in the high voltage area 203. A distance between the first contact member 201 and the second contact member 202 may be a preset safety distance. For example, the distance is greater than or equal to a creepage distance that is defined as the shortest distance over surface between two conductive parts, so as to prevent a distance between the two contact members from being less than the creepage distance and cause discharge between the positive electrode and the negative electrode. The low voltage area 204 can be used to connect other electronic components, and the high voltage base board 20 in embodiments of the present disclosure does not need to be provided with additional high voltage boards and low voltage boards, which can have a simple structure and save costs.

In some other embodiments, a spacer may be provided between the high voltage area 203 and the low voltage area 204, and a spacer may be provided between the first contact member 201 and the second contact member 202, which can also prevent discharge between the positive electrode and the negative electrode. In an embodiment of the present disclosure, the spacer includes a board with a certain height formed of an insulating material.

The crystal 215 of the detector in embodiments of the present disclosure is placed between the cathode and the anode, and a bias high voltage of thousand volts is applied between the cathode and the anode to form an electric field. The photons irradiate the cathode and transfer their own energy to the electrons of the crystal 215, and the electrons drift toward the anode. In response, the anode generates an electrical signal. Downstream the detector, a back-end pulse shaper circuit processes the electrical signal and generates a pulse with a peak amplitude indicative of the energy of the detected photon, and then a pulse discriminator circuit compares the peak amplitude of the pulse with an energy threshold. For each energy threshold, a counter counts the number of pulses corresponding to the energy within the energy threshold. An energy splitter can analyze photons from the energy perspective, and split the counts to obtain splitting data. An image reconstruction device reconstructs the splitting data by using a spectrum reconstruction algorithm, so as to obtain a multi-energy spectrum image. In some embodiments, the back-end pulse shaper circuit, the pulse discriminator circuit, the counter, and the energy splitter can be implemented inside a chip for data readout. The image reconstruction device can be implemented by software and implemented in an image reconstruction system.

The embodiments of the present disclosure provide high voltage assemblies, by providing the crystal 215 on the crystal substrate 212, coupling the high voltage cathode board 216 to the crystal 215, coupling the crystal substrate 212 and the high voltage cathode board 216 to the high voltage base board 20, and applying a bias high voltage to the crystal 215 by the high voltage base board 20. The structure is simple. The first connection member 210 is configured to shift relative to the first contact member 201 in response to a force, and the second connection member 211 is configured to shift relative to the second contact member 202 in response to a force. The configuration of the first connection member 210 and the second connection member 211 can thereby prevent a distance between the first connection member 210 of the individual sub-detector 21 and the first contact member 201 of the high voltage base board 20 or a distance between the second connection member 211 of the individual sub-detector 21 and the second contact member 202 of the high voltage base board 20 from changing due to a manufacturing tolerance or a slight position change, and thus avoid a situation that the connection member and the contact member cannot be contacted. The configuration effectively ensures that all sub-detectors 21 can be in stable electrical contact with the high voltage base board 20, and effectively ensures the quality of the image.

The above description is merely preferred examples of the present application and is not intended to limit the present application in any form. Although the present application is disclosed by the above examples, the examples are not intended to limit the present application. Those skilled in the art, without departing from the scope of the technical scheme of the present application, may make a plurality of changes and modifications of the technical scheme of the present application by the method and technical content disclosed above. Therefore, without departing from the scope of the technical scheme of the present application, based on technical essences of the present application, any simple alterations, equal changes and modifications should fall within the protection scope of the technical scheme of the present application. Accordingly, other embodiments are within the scope of the following claims.

What is claimed is:

1. A high voltage assembly, comprising:
a high voltage base board; and
a plurality of sub-detectors configured to be in electrical contact with the high voltage base board, each of the plurality of sub-detectors comprising:
a crystal substrate,
a crystal coupled to an anode of the crystal substrate,
a high voltage transfer board coupled to the crystal substrate, and
a high voltage cathode board configured to couple the crystal with the high voltage transfer board,
wherein one of the high voltage transfer board and the high voltage base board comprises a first connection member and a second connection member, and the other one of the high voltage transfer board and the high voltage base board comprises a first contact member and a second contact member,
wherein the first connection member is configured to shift relative to the first contact member in response to a first force, and the second connection member is configured to shift relative to the second contact member in response to a second force, and
wherein the high voltage transfer board and the high voltage base board are configured to be in electrical contact with the first contact member through the first connection member and are configured to be in electrical contact with the second contact member through the second connection member, such that a high voltage is applied at both ends of the crystal.

2. The high voltage assembly according to claim 1, wherein the crystal comprises a cadmium telluride (CdTe) crystal or a cadmium zinc telluride (CZT) crystal.

3. The high voltage assembly according to claim 1, wherein the sub-detector further comprises a data acquisition board coupled to the crystal substrate.

4. The high voltage assembly according to claim 3, wherein the crystal substrate comprises an ASIC (Application Specific Integrated Circuit) chip configured to acquire and process a pulse signal and transmit the pulse signal to the data acquisition board.

5. The high voltage assembly according to claim 3, wherein the sub-detector further comprises a support configured to support the crystal substrate, the high voltage transfer board, and the data acquisition board.

6. The high voltage assembly according to claim 3, wherein the sub-detector further comprises a high voltage connection component,
wherein the high voltage transfer board comprises the first connection member and the second connection member, the high voltage cathode board is coupled with the first connection member through the high voltage connection component, and the crystal substrate is coupled with the second connection member through the data acquisition board, and wherein the first connection member is coupled to a cathode of the high voltage base board, and the second connection member is coupled to an anode of the high voltage base board.

7. The high voltage assembly according to claim 1, wherein the high voltage cathode board comprises a bare electrode arranged on a first side of the high voltage cathode board and an insulating material arranged on a second side of the high voltage cathode board.

8. The high voltage assembly according to claim 7, wherein the bare electrode is attached to the crystal, and the high voltage cathode board is made of a soft conductive material.

9. The high voltage assembly according to claim 8, wherein the soft conductive material comprises a first film and a second conductive metal film that are laminated together, and wherein the second conductive metal film is attached to the crystal.

10. The high voltage assembly according to claim 1, wherein at least one of the first contact member or the second contact member comprises an electrically conductive pad.

11. The high voltage assembly according to claim 10, wherein the at least one of the first connection member or the second connection member comprises a Pogo Pin terminal or an elastically deformable elastic terminal.

12. The high voltage assembly according to claim 10, wherein the high voltage base board comprises a high voltage area and a low voltage area, and wherein the high voltage base board comprises the first contact member and the second contact member, and the first contact member and the second contact member are arranged in the high voltage area.

13. The high voltage assembly according to claim 12, further comprising a spacer made of an insulating material, wherein the spacer is provided between the first contact member and the second contact member.

14. A detector, comprising:
a cradle; and
a high voltage assembly comprising:
a high voltage base board fixed to the cradle; and
a plurality of sub-detectors configured to be in electrical contact with the high voltage base board, each of the plurality of sub-detectors comprising:
a crystal substrate,
a crystal coupled to an anode of the crystal substrate,
a high voltage transfer board coupled to the crystal substrate, and
a high voltage cathode board configured to couple the crystal with the high voltage transfer board,
wherein one of the high voltage transfer board and the high voltage base board comprises a first connection member and a second connection member, and the other one of the high voltage transfer board and the high voltage base board comprises a first contact member and a second contact member, wherein the first connection member is configured to shift relative to the first contact member in response to a first force, and the second connection member is configured to shift relative to the second contact member in response to a second force, wherein the high voltage transfer board and the high voltage base board is configured to be in electrical contact with the first contact member through the first connection member and is configured to be in electrical contact with the second contact member through the second connection member, such that a high voltage is applied at both ends of the crystal, and wherein one of the cradle and the sub-detector comprises a hole, and the other one of the cradle and the sub-detector comprises a protrusion that matches with the hole, and the sub-detector is fixed to the cradle through the hole and the protrusion.

15. The detector according to claim 14, wherein the sub-detector further comprises a data acquisition board coupled to the crystal substrate.

16. The detector according to claim 15, wherein the sub-detector further comprises a high voltage connection component, wherein the high voltage transfer board comprises the first connection member and the second connection member, the high voltage cathode board is coupled with the first connection member through the high voltage connection component, and the crystal substrate is coupled with the second connection member through the data acquisition board, and wherein the first connection member is coupled to a cathode of the high voltage base board, and the second connection member is coupled to an anode of the high voltage base board.

17. The detector according to claim 14, wherein the high voltage cathode board comprises a bare electrode arranged on a first side of the high voltage cathode board, and an insulating material arranged on a second side of the high voltage cathode board.

18. The detector according to claim 17, wherein the bare electrode is attached to the crystal, and the high voltage cathode board is made of a soft conductive material.

19. The detector according to claim 14, wherein at least one of the first contact member or the second contact member comprises an electrically conductive pad.

20. The detector according to claim 19, wherein the at least one of the first connection member or the second connection member comprises a Pogo Pin terminal or an elastically deformable elastic terminal.

* * * * *